United States Patent [19]

Raemer

[11] Patent Number: 5,320,093
[45] Date of Patent: Jun. 14, 1994

[54] RAPID ANESTHESIA EMERGENCE SYSTEM USING CLOSED-LOOP $PCO_2$ CONTROL

[75] Inventor: Dan Raemer, Brookline, Mass.

[73] Assignee: Brigham and Women's Hospital, Boston, Mass.

[21] Appl. No.: 632,002

[22] Filed: Dec. 21, 1990

[51] Int. Cl.$^5$ .............................................. A61M 15/00
[52] U.S. Cl. ........................... 128/203.12; 128/204.18; 128/204.23; 128/914
[58] Field of Search ....................... 128/204.18, 204.21, 128/204.23, 205.17, 914, 203.12, 205.11

[56] References Cited

U.S. PATENT DOCUMENTS

| | | | |
|---|---|---|---|
| 2,817,350 | 12/1957 | Bradner et al. | 137/87 |
| 3,593,735 | 9/1968 | Reiher | 137/88 |
| 3,805,590 | 4/1974 | Ringwall et al. | 73/24 |
| 3,895,630 | 7/1975 | Bachman | 128/203.12 |
| 3,910,261 | 10/1975 | Ragsdale et al. | 128/204.21 |
| 3,972,327 | 8/1976 | Ernst et al. | 124/719 |
| 4,112,938 | 9/1978 | Jeretin | 128/204.23 |
| 4,121,581 | 10/1978 | Schmader | 128/718 |
| 4,211,221 | 7/1980 | Schwanbom et al. | 128/204.26 |
| 4,233,842 | 11/1980 | Raemer et al. | 73/861.04 |
| 4,269,194 | 5/1981 | Rayburn et al. | 128/719 |
| 4,326,513 | 4/1982 | Schulz et al. | 128/203.14 |
| 4,362,154 | 12/1982 | Le Masson | 128/204.22 |
| 4,423,739 | 1/1984 | Passaro et al. | 128/719 |
| 4,440,177 | 4/1984 | Anderson et al. | 128/719 |
| 4,537,190 | 8/1985 | Caillot et al. | 128/204.22 |
| 4,637,385 | 1/1987 | Rusz | 128/204.21 |
| 4,648,396 | 3/1987 | Raemer | 128/204.22 |
| 4,651,729 | 3/1987 | Rae | 128/203.14 |
| 4,838,257 | 6/1989 | Hatch | 128/204.18 |

Primary Examiner—Edgar S. Burr
Assistant Examiner—Aaron J. Lewis
Attorney, Agent, or Firm—Sterne, Kessler, Goldstein & Fox

[57] ABSTRACT

A system is disclosed for rapidly restoring ventilatory drive to an anesthetized patient after surgery. The end-expired carbon dioxide partial pressure is used as feedback to determine the amount of $CO_2$ to be added to the inspired breathing mixture of the patient's breathing circuit. The $CO_2$ added to the patient's breathing circuit increases $CO_2$ within the blood stream to a level sufficient to stimulate the central ventilatory center in the brain, thereby rapidly restoring ventilatory drive to the patient.

21 Claims, 4 Drawing Sheets

RAPID ANESTHESIA EMERGENCE SYSTEM USING CLOSED-LOOP PCO₂ CONTROL

FIELD OF THE INVENTION

The invention relates generally to a $CO_2$ feedback system and more particularly to a system for rapidly restoring the ventilatory drive of an anesthetized patent.

BACKGROUND OF THE INVENTION

Anesthesia is the loss of sensation in the body induced by the administration of a drug. There are many risks associated with the drug-induced loss of sensation and without proper equipment and skilled operators, complications often occur. Because there are risks associated with anesthesia, it is preferable that an anesthetized patient emerge from anesthesia and that ventilatory drive be restored as soon as possible.

The ability of patients to breathe on their own upon emergence from anesthesia is dependent upon three conditions. First, the blood concentration of anesthetic agent must be low, less than about 0.2% for isoflurane. This is achieved by turning off the anesthetic agent, washing the agent from the breathing circuit, and ventilating the patient with a normal minute volume for several minutes. "Minute volume" is the total volume of gas delivered to or expired by a patient over one minute. Hyperventilation can be used to accelerate the process of removing the anesthetic agent from the body. However, hyperventilation causes $CO_2$ to be expired from the lung and lowers the partial pressure of $CO_2$ ($PCO_2$) in the blood, $P_aCO_2$ (arterial blood carbon dioxide tension).

Second, if a neuromuscular function blocking drug had been used, it must be adequately reversed for sufficient ventilatory muscle strength to return. This is accomplished pharmacologically.

Third, the $P_aCO_2$ must be high enough to adequately stimulate the central ventilatory center in the brain. The ventilatory response to $CO_2$ is a continuous function, but, a $P_aCO_2$ between 35 mmHg and 44 mmHg is normally required to stimulate ventilatory efforts in the patient recovering from anesthesia.

Unfortunately, increasing $P_aCO_2$ by hypoventilation can lead to complications such as hypoxia. Also, the awakening process is actually prolonged by the failure to remove anesthetic agent from the patient's body. Thus, the clinician is faced with a dilemma; the clinician must both remove the anesthetic agent by hyperventilation and increase the arterial blood carbon dioxide tension, $P_aCO_2$, by hypoventilation.

Some anesthesia machines have been manufactured with a valve that allows bypassing the $CO_2$ absorber in a circle system breathing circuit. Bypassing the $CO_2$ absorber permits the patient to rebreath expired $CO_2$ gases thus the $PCO_2$ rises in the inspired gas. However, this does not substantially hasten awakening because if the system is mostly closed, anesthetic agent is also recirculated to the patient. Therefore, even though the patient is able to rebreath expired $CO_2$ and thereby increase the arterial blood carbon dioxide tension, the patient also rebreaths expired anesthesia agent. If the system was mostly open, little rise in $PCO_2$ can be achieved. Also, such a design requires the clinician to remember to shut off the bypass, before the next procedure. Failure to turn off the bypass, however, was not an infrequent occurrence and occasionally contributed to complications.

In order to increase the $P_aCO_2$ of a patient, it is helpful to measure $P_aCO_2$. While measurements of $CO_2$ from the expired breathing gas have long been used to estimate the $P_aCO_2$, this information has not been used to rapidly restore ventilatory drive to a patient after anesthesia. The gas at the end of each tidal ventilation is assumed to be in equilibrium with the arterial blood. Hence, the end-tidal $CO_2$ partial pressure, $P_{ET}CO_2$, is often used to estimate $P_aCO_2$. For example, U.S. Pat. No. 4,423,739 to Passaro et al. discloses an apparatus for determining the partial pressure of $CO_2$ in the arterial blood of a patient by measuring carbon dioxide concentration at the end-tidal of a patient's exhaled breath.

The practice of using the partial pressure of $CO_2$ in the arterial blood of a patient to control respiration has been in use for several years. For example, U.S. Pat. No. 4,112,938 to Jeretin discloses a device for controlling patient respiration in accordance with the partial pressure of $CO_2$ in the arterial blood or tissue measured in the alveolar expiration air. The Jeretin patent states that low arterial $CO_2$ content resulting from hyperventilation is brought to a standard value by increasing $CO_2$ content in the inspiration air. The $CO_2$ in this system comes, however, from the patient's own expired gas, not from an external source. Control of this process is based on a continuous measuring of the partial pressure of $CO_2$. The serious problems associated with anesthesiology and in particular restoring the ventilatory drive of a patient are not addressed by the Jeretin patent.

Previous attempts to restore the ventilatory drive to an anesthetized patient involves such things as bypassing the $CO_2$ absorber. This technique, while partially effective in raising the $CO_2$ in the inspired mixture has the problem of reintroducing the anesthesia agent to the patient. For example, in the Jeretin device, the patient rebreathes anesthetic agent as well as the $CO_2$. Such a process inhibits resuscitation of the patient. It is one object of the present invention to solve this problem. Furthermore, as rebreathing limits the inspired $PCO_2$ to the patient's mean expired $PCO_2$, the $CO_2$ concentration may not be high enough to raise the $P_aCO_2$ to the desired level rapidly and reliably. It is the object of the present invention to also solve this problem. Yet another object of the invention is to provide a system which is automated to enable effective emergence from anesthesia while minimizing the risk of operator error. It is yet a further object of the invention to optimize the introduction of $CO_2$ to a patient to minimize risks and complications associated with prolonged anesthesia.

SUMMARY OF THE INVENTION

To achieve the foregoing and other objects, and in accordance with the purposes of the present invention as embodied and broadly described herein, the method for restoring ventilatory drive to an anesthetized patient of the present invention includes the step of measuring the end-tidal value of the respiratory partial pressure of carbon dioxide $P_{ET}CO_2$ of the anesthetized patient. The next step in the method is to estimate the partial pressure of carbon dioxide within the blood stream of the patient ($P_aCO_2$) using the measured end-tidal value of the respiratory partial pressure of carbon dioxide. The estimated $P_aCO_2$ is then compared with a reference value to determine whether $CO_2$ is to be added to the breathing circuit and the amount to be added. Finally, $CO_2$ is added directly to the breathing circuit of the patient in the amount determined.

In one aspect of the invention a flow meter is used to detect the phases of the respiratory cycle to differentiate between expired end-tidal $CO_2$ and the increase in $CO_2$ partial pressure due to the addition of $CO_2$ into the breathing circuit.

In yet another aspect of the invention, the addition of $CO_2$ into the breathing circuit is inhibited if the average inspired $CO_2$ concentration exceeds a reference value.

Another aspect of the invention is the device used for restoring ventilatory drive to an anesthetized patient. The device of the present invention includes a device for determining the partial pressure of carbon dioxide in the bloodstream of a patient, and a feedback control system which utilizes the partial pressure of carbon dioxide in the bloodstream to control the addition of $CO_2$ into the inspiration line of the breathing circuit of an anesthetized patient.

BRIEF DESCRIPTION OF THE DRAWINGS

The accompanying drawing, which is incorporated in and forms a part of the specification, illustrates the present invention, and together with the written description, serves to explain the principles of the invention. In the drawing.

DESCRIPTION OF THE PREFERRED EMBODIMENT

Figure 1:
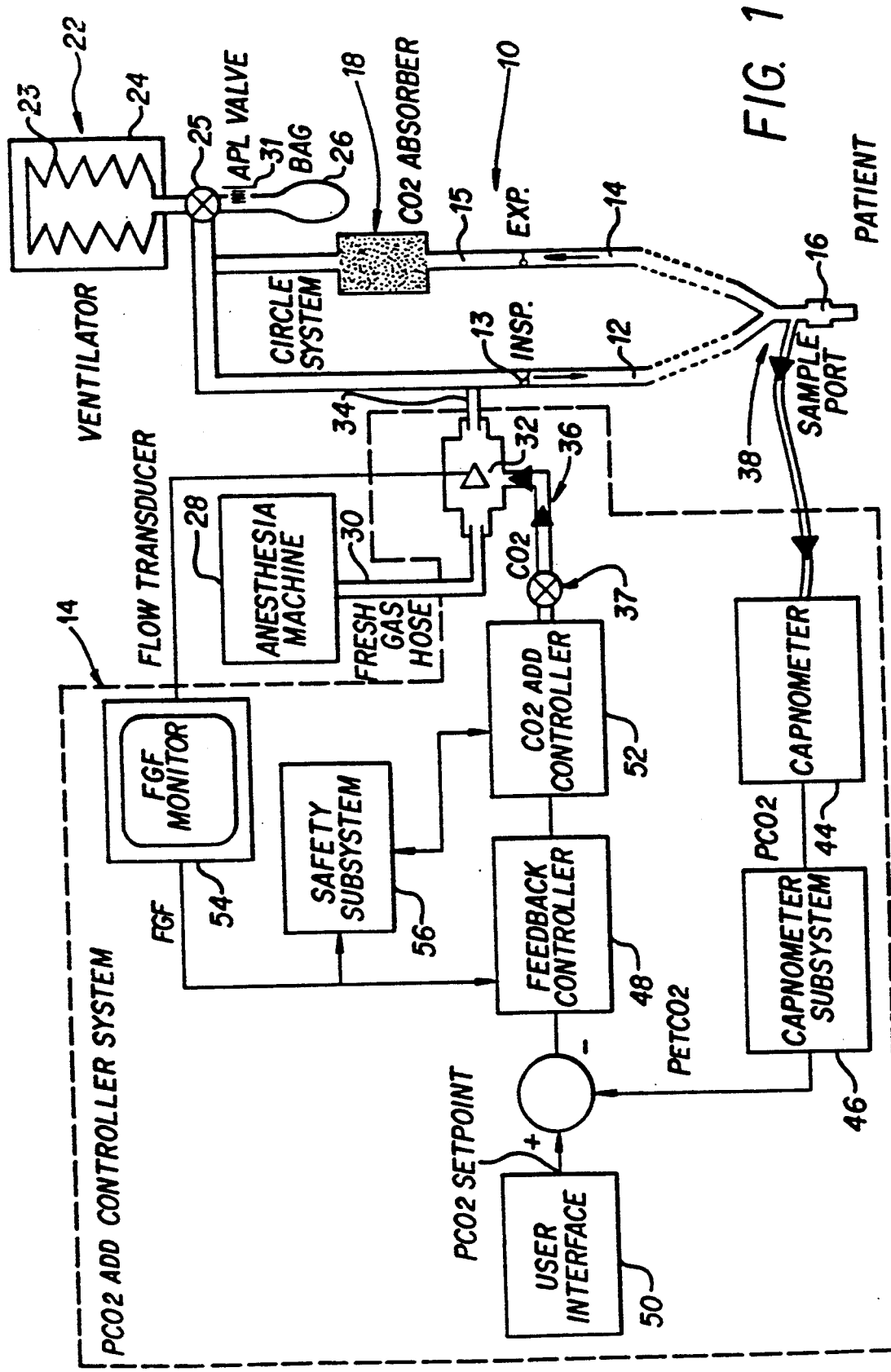
FIG. 1 is a schematic representation of the feedback control system of the present invention.

The present invention is a device and method for rapidly restoring ventilatory drive to a patient after anesthesia. While the invention can be embodied in various different manners, the following description of the invention helps to exemplify one preferred prescription for carrying out the practice of the invention. FIG. 1, appended hereto, is a schematic representation of a prefered embodiment of the invention.

Refering to FIG. 1, a breathing circuit commonly known as the "anesthesia circle system," identified generally as 10, includes a number of features which are generally known in the art. The breathing circuit includes an inspiration line 12 and an expiration line 14. The inspiration line 12 is the conduit in the breathing circuit by which gases are delivered to a patient. Within the inspiration line 14 is a one-way inspiration valve 13 which assures that the flow of gas through the inspiration line 12 is unidirectional. Gases and vapors (for example anesthesic vapors entrained with ventilation gases) may be delivered to a patient (not shown) via port 16.

The breathing circuit 10 further includes an expiration line 14 for receiving expired gases from the patient. Within the expiration line is a one-way expiration valve 15 for preventing exhaled gases from being reintroduced to a patient.

A $CO_2$ absorber 18 is located downstream of the one-way expiration valve 15. The $CO_2$ absorber is located in the circuit in order to make rebreathing in the close-circuit possible. A prefered $CO_2$ absorber for use in breathing circuit 10 is one which has a lack of toxicity with common anesthetic, low air flow impedence, efficiency in removing $CO_2$, and ease of handling. Two possible $CO_2$ absorbers include soda lime (94% calcium hydroxide, 5% sodium hydroxide, and 1% potassium hydroxide as an activator; with small amounts of silica added) and baralyme (80% calcium hydroxide, and 20% barium hydroxide). The process of absorption using soda lime or baralyme is a chemical process and not a physical one. $CO_2$ absorbers are a well known component of a breathing circuit for anesthesia and that any known $CO_2$ absorber can be used as a substitute for the specific chemical absorbers described above.

Expired gases passing through $CO_2$ absorber 18 are recirculated and entrained with other gases and passed back through the inspiration line 14, to the patient.

A ventilator 22 is used in conjuction with the invention to deliver gas to a patient. Any conventional ventilator 22 may be used when practicing the invention. Typically, ventilator 22 will include breathing bellows 23 located within a clear plastic receptacle 24. The schematical representation of the ventilator does not show details because ventilators are well known. Generally, bellows 23 of ventilator 22 separates a driving gas circuit from a patient gas circuit. The driving gas is located between the bellows 23 and the receptacle 24. During the phase of the cycle when the patient is inspiring gases, the driving gas exerts force on the bellows 23, causing the anesthetic gas within the bellows 23 to be delivered to a patient. During the expiration phase, the driving gas is vented to the atmosphere through a relief valve (not shown). Thereafter, anesthetic gas which is in the breathing circuit fills the bellows. Excess gas is vented through a relief valve (not shown) when the bellows 23 are full; vented excess gases may include both fresh gas and expired gas. As stated above, any anesthesia ventilator may be used to practice the invention including pneumatic and electronic ventilators.

An anesthesiologist also has the option of providing ventilation manually from the bag 26. Selector valve 25 is used to select between manual ventilation or ventilation via the ventilator 22. During manual ventilation, most of the expired gas and fresh gas fills the bag 26. The anesthesiologist then squeezes the bag to provide positive pressure for inspiration. An adjustable pressure limiting (APL) valve 31 may be built into the same assembly as the selector valve 25 or may be in a separate assembly. The APL valve 31 limits the maximum pressure in the circuit during manual ventilation. It is especially important to limit the maximum pressure during manual operation as a hard squeeze on bag 26 could subject the patient's lungs to an excessive pressure. It is also important to limit the maximum pressure during expiration because a high flow of fresh gas into the circuit could raise the pressure to an unsafe level.

Also used in conjunction with the present invention is a standard anesthesia machine 28 which delivers fresh gas to the breathing circuit 10. An anesthesia machine may, for example, properly mix oxygen ($O_2$) with nitrous oxide ($N_2O$) for delivery to a patient. A generic anesthesia machine may include a supply of nitrous oxide which passes through a pressure regulator, a fail-safe device and a flow meter. The flow of nitrous oxide through the flow meter is controlled by a valve. Similarly, a supply of oxygen passes through an oxygen pressure regulator, to an oxygen flowmeter. After passing the nitrous oxide and the oxygen through flow meters, one for each gas, the gases are entrained and passed through one of a series of calibrated vaporizers. The resultant gas then exits the anesthesia machine through fresh gas hose 30.

The present invention is a control system which introduces $CO_2$ gas into breathing circuit 10 during emergence from anesthesia. Instead of providing a bypass of the $CO_2$ absorber, as has been previously attempted, $CO_2$ gas is delivered directly into the inspiration line 12 of breathing circuit 10. The present invention is a negative feedback control system and method which utilizes the partial pressure of the end tidal $CO_2$ expired by a patient ($P_{ET}CO_2$) to control the quantity of $CO_2$ which is delivered to inspiration line 12 of breathing circuit 10. In the embodiment of the invention shown in FIG. 1, $CO_2$ gas is passed through a $CO_2$ hose 36 into a mixing zone 32 for delivery into breathing circuit 10 via delivery hose 34. Carbon dioxide is delivered directly into the inspiration line 12 and thus increases the partial pressure of $CO_2$ in the blood to a level adequate to stimulate the central ventilatory center of the brain. A pair of time-controlled valves 37 can be used to determine the amount of time that $CO_2$ is added to the inspired line 12. Furthermore, the proportion of time of $CO_2$ addition can also be controlled through duty cycle control. During duty cycle control, the ratio of on-time to off-time can be controlled by rapidly turning valve 37 on and off. The valves 37 are controlled by controller 52. Valves 37 and the $CO_{2ADD}$ controller 52 are described in greater detail later in the specification.

One of ordinary skill in the art will appreciate that other available techniques may be used for measuring the partial pressure of $CO_2$ in a patient's bloodstream. For example, there are commerically available devices that may also be used in the invention which analyze blood directly. These devices, called continuous blood gas analyzers, typically use electrochemical or electro-optical sensors to perform this function.

As stated above, the ability of a patient to breathe on their own after anesthesia is a function of several variables. One of these variables is the concentration of anesthesia agent in the blood of the patient. The blood concentration of the anesthesia agent must be low in order for the patient to breathe on his/her own. This is acheived by turning off the anesthesia agent, washing the agent from breathing circuit 10 and ventilating the patient. Hyperventilation helps accelerate the process of removing anesthesia agent from the patient. Because hyperventilation causes carbon dioxide to be expired from the lungs, lowering the partial pressure of carbon dioxide in the blood, the invention introduces carbon dioxide directly into the breathing circuit to counteract the lowering of carbon dioxide in the blood due to hyperventilation.

The $PCO_{2add}$ contoller system is designated generally by reference number 42 and is deliniated in FIG. 1 by a broken line. The controller system 42, also refered to hereinafter as the feedback control system, includes a number of subcomponents or subsystems which are used to practice the invention.

Broadly, the invention measures the partial pressure of carbon dioxide being expired by a patient. Using this measurement of the end tidal partial pressure of carbon dioxide $P_{ET}CO_2$, the partial pressure of carbon dioxide in the patient's blood (the arterial blood carbon dioxide tension) $P_aCO_2$ can be estimated. The end tidal pressure of carbon dioxide is used to estimate $P_aCO_2$. The value of $P_aCO_2$ is then compared with a reference value. If the reference value, generally the desired $PCO_2$ value, exceeds the estimated value of $P_aCO_2$, then carbon dioxide is introduced into the inspiration line of the breathing circuit at a rate which is a function of the measured difference between the reference amount and the end tidal pressure of carbon dioxide. The subcomponents of the present invention are described in detail below.

Expired gas is tapped from the breathing circuit 10 through a sample port 38. A capnometer 44, such as is commercially available, is used to measure the respiratory partial pressure of carbon dioxide (or carbon dioxide concentration). The capnometer may measure the carbon dioxide concentration by measuring the amount of infrared radiation absorbed by carbon dioxide molecules. A particular review band of wavelength measured for this purpose is around 4.25 microns. Alternatively, the principle of operation of the capnometer may be Raman spectroscopy, mass spectroscopy, acoustic spectroscopy, or gas chromatography. Furthermore, a capnometer using a curvette mounted directly in line with the breathing circuit may also be used. Such a capnometer does not require a sample port 38 but is mounted directly on the curvette. The curvette is ordinarily mounted where sample port 38 would come into the circuit.

In the operation of a capnometer 44 using Raman spectroscopy as its principle of operation, a beam of light passes through the gas medium. A certain portion of the light passing through the sample is absorbed, a certain portion is transmitted (passes through the sample), and a certain portion is scattered. Some of the light which is scattered undergoes a shift in frequency or wavelength as the light is scattered; this is a characteristic of the gas molecules. The shift occurs because of a loss in energy as a result of the collision with the gas medium. The intensity of Raman scattered light at specific frequencies gives a measure of the concentration of gas constituents.

Mass spectroscopy separates components on the basis of mass and charge rather than physical characteristics. By contrast gas chromatography first separates the components of a gas mixture and then measures their individual concentrations.

The capnometer sub-system 46 measures $P_{ET}CO_2$ using a commercial instrument and reports the raw signal to a computer. An algorithm processes the signal to measure $P_{ET}CO_2$ in the presence of inspired $CO_2$. This is necessary because the algorithms in commercial capnometers cannot measure $P_{ET}CO_2$ when the inspired $PCO_2$ is higher than a few mm Hg or when pulses of $CO_2$ appear during inspiration. The output from capnometer subsystem 46 goes directly to the feedback controller 48 to be compared to a reference. The measured $P_{ET}CO_2$ is displayed to the user.

A feedback controller 48 compares the measured and reference point $P_{ET}CO_2$. The feedback compensation is designed to produce a stable control response, zero-steady state error, and limited overshoot. Although the feedback is principally adaptive as a function of minute ventilation, the system may also be adaptive as a function of tidal volume, respiratory rate or the type of circuit in general. Also, it may be necessary to use a crude measure of fresh gas flow to optimize the system response. The feedback is designed to be tolerant of missing or artifactual data.

The user interface 50 allows the physician or operator to enter data into the controller 48 via a PC computer. Principally, a set-point for $P_{ET}CO_2$ may be chosen. The display provides data to the physician or operator informing him/her of system status, $P_{ET}CO_2$ set-point, measured $P_{ET}CO_2$, fresh gas flow status, and $CO_{2ADD}$ flow.

The $CO_{2ADD}$ controller 52 interfaces the feedback controller signal to the flow of $CO_2$ into the fresh gas. The desired $CO_{2ADD}$ control signal is converted to drive the pair of time-controlled valves 37 which are pneumatically connected in series. The time-controlled valves 37 are preferably solenoid valves although one of ordinary skill will appreciate that other types of valves may also be used. The valves 37 are switched open and closed approximately once per second. The proportion of time the valves 37 are open relative to the time the valves are closed is in proportion to the control signal. When the valves 37 are open, the flow of $CO_2$ gas is allowed to pass into the fresh gas line. Two valves 37 are used instead of one as a safety measure. If one valve malfunctions in the open position, the other valve will prevent the unabated flow of $CO_2$ into the fresh gas flow. The opening and closing of each of the two valves 37 are controlled by an independent digital electronic circuit. As a safety measure, the logic of the digital circuits is designed so that the removal or open-circuit failure of any of the components results in a control signal to its respective valve 37 which renders it closed. The $CO_2$ is provided to the valves 37 from a precision two-stage pressure regulator and series linear fluid resistor. These components limit the total flow of $CO_2$ to approximately 500 ml/min as a safety measure. In addition, a pressure relief valve between the pressure regulator and the fluid resistor limits the pressure to a safe level should the regulator fail. Also, a flow transducer in series with the gas flow control components may be used to command the solenoid valves to close if a component failure causes excessive gas flow.

A Fresh Gas Flow Monitor (FGFM) 54 is a series component of the system and measures total fresh gas flow to the breathing circuit. The FGFM is a self-heated thermistor flow meter with an accuracy of about $\pm 20\%$. The FGFM is a safety feature which assures that pure or concentrated $CO_2$ is not added to the circuit accidentally. It is important for the added $CO_2$ to mix with fresh gas. The signal from this transducer is used to disable the $CO_{2ADD}$ system when the fresh gas flow is below a certain value (e.g., 1 L/min). Also, the FGFM signal may be used to adapt the feedback parameters of the controller to refine the system dynamic response. There are commercially available flow meters which would be suitable as an FGFM. The principle of operation of a suitable FGFM could be any among thermal transport, momentum (vane), vortex precession, or Poiseuille's law, among others.

The present invention can be optimized and varied without departing from the above described general principle of providing a feedback control system which introduces $CO_2$ into the inspired mixture of a patient as a function of the end tidal value of the respiratory $PCO_2$. For example the invention can be refined by introducing $CO_2$ into the inspired mixture only during the inspiration cycle of the patient. To accomplish this end, a flow meter can be used for detecting the phases of the respiratory cycle. $CO_2$ gas can then be added to the inspired mixture in concert with the desired phase (such as the inspiration phase).

In one preferred embodiment of the invention, the $CO_2$ waveform which is measured by capnometer 44 can be processed to differentiate between the expired peak value which is attainable to the expiration of $CO_2$ gases by a patient and inspired peak value which is produced as a result of additional $CO_2$ being added to the breathing circuit. Both inspired and expired gases are being tapped via sample port 38. Therefore, it is important to distinguish the source of the $CO_2$. By processing the $CO_2$ waveform, an accurate estimate of $P_aCO_2$ can be established.

Utilizing a PID (Proportional-Integral-Derivative) controller, the present invention measures the $P_{ET}CO_2$ and computes a feedback compensation value which is related to the difference between the desired and measured $P_{ET}CO_2$. The flow rate of the $CO_2$ gas which is added to the breathing mixture of a patient is controlled by an electronic signal. The output which controls the flow rate of the added $CO_2$ gas is a function of the sum of three terms:

$$Y(t) = C_1 \cdot E(t) + C_2 E(t)dt + C_3 \frac{C_3 E(t)}{dt} ;$$

where Y(t) is the output signal, $C_1$, $C_2$ and $C_3$ are constants, E(t) is the error (difference between the desired $P_{ET}CO_2$ and the measured $P_{ET}CO_2$) and dE(t)/dt is the time derivative of E(t). The output may be adjusted by a constant of proportionality as circumstance may dictate.

It is also possible to use the patients minute ventilation, tidal volume, or respiratory rate to modify one or more of the terms in the above circuit equation. The patients minute ventilation, tidal volume or respiratory rate may be measured using any well-known technique. For example, these measurements may be made based if the on thermal dissipation, a pressure difference across a resistive element (pneumotachograph), the rotation rate of a vane, or the oscillation frequency of a fluid vortex.

Figure 2:
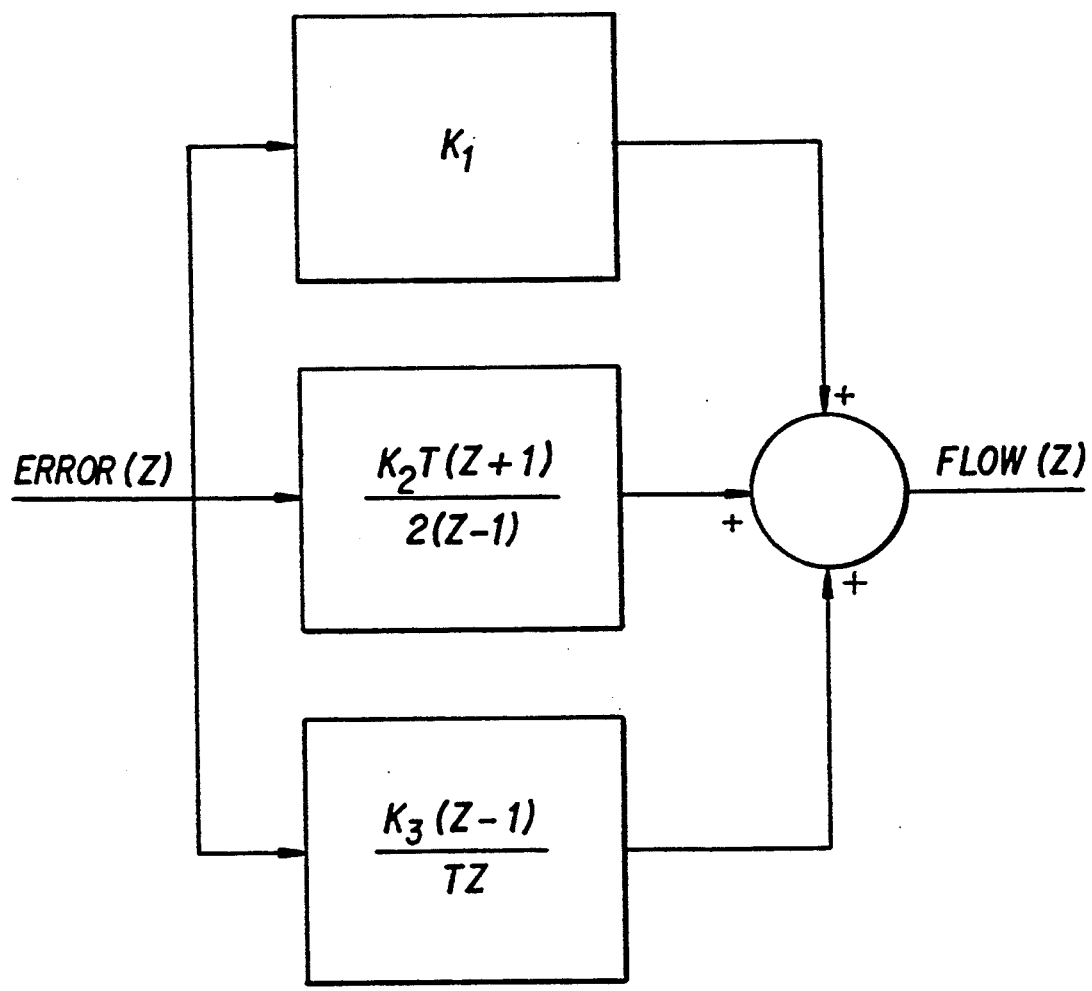
FIG. 2 is a block diagram of a digital PID controller used in the feedback control system of the present invention.

Although the above is an analog implementation of a feedback controller, it is also possible to use a sampled-data equivalent of a feedback controller. This is commonly used with microcomputers. The block diagram of the digital PID controller is shown in FIG. 2. The microcomputer samples the input variable (error between a desired and a measured $CO_2$) periodically (every T seconds). Computer software is used to mathematically implement the feedback algorithm described above. A listing of the computer code is appended to this specification.

While the output of the digital controller is presented every T seconds, a circuit element called a zero-order-hold takes the periodically produced output, holds it steady and implements the output action of adding $CO_2$.

In the block diagram of the digital PID controller in FIG. 2, K, $K_2$ and $K_3$ are coefficients of the proportional integral and derivative terms, respectively. T is the sample time interval, k is an integer number of sample intervals, and Z is the Z-transform operator. Note that $K_1$, $K_2$ and $K_3$ serve the same purpose as $C_1$, $C_2$ and $C_3$ in the analog implementation discussed previously; however, the values of $K_1$, $K_2$ and $K_3$ may be different from $C_1$, $C_2$ and $C_3$.

The transfer function of the digital PID controller is as follows:

$$\frac{Y(nT)}{E(nT)} = K_1 \frac{K_2 T(Z + 1)}{2(Z - 1)} + \frac{K_3(Z - 1)}{TZ}$$

Figure 3:
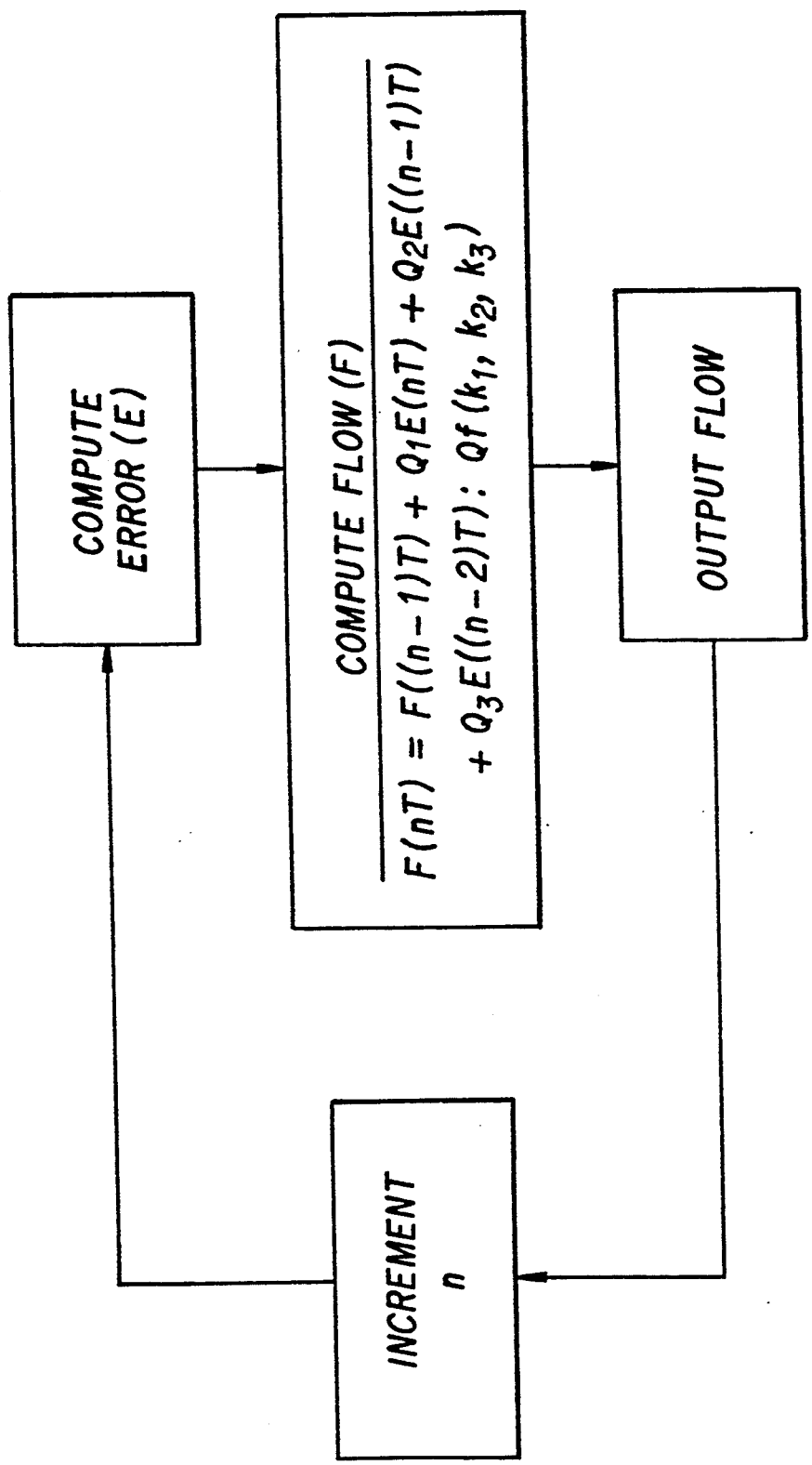
FIG. 3 is a block diagram of flow computation within the feedback control system of the present invention.

A block diagram of this process is shown in FIG. 3. The values of the coefficients as shown in FIG. 3 are dependent on the characteristics of the design of the system which is being controlled. The increment (n), error (E), flow (F) and the output are functions of the volume and flow characteristics of the breathing circuit, the patient's lung and $CO_2$ transfer characteristics, and the settings of the ventilator and anesthesia machine. Furthermore, design goals such as tolerable overshoot, time to achieve control and accuracy of control are used to determine the value of coefficients $K_1$, $K_2$ and $K_3$.

Figure 4:
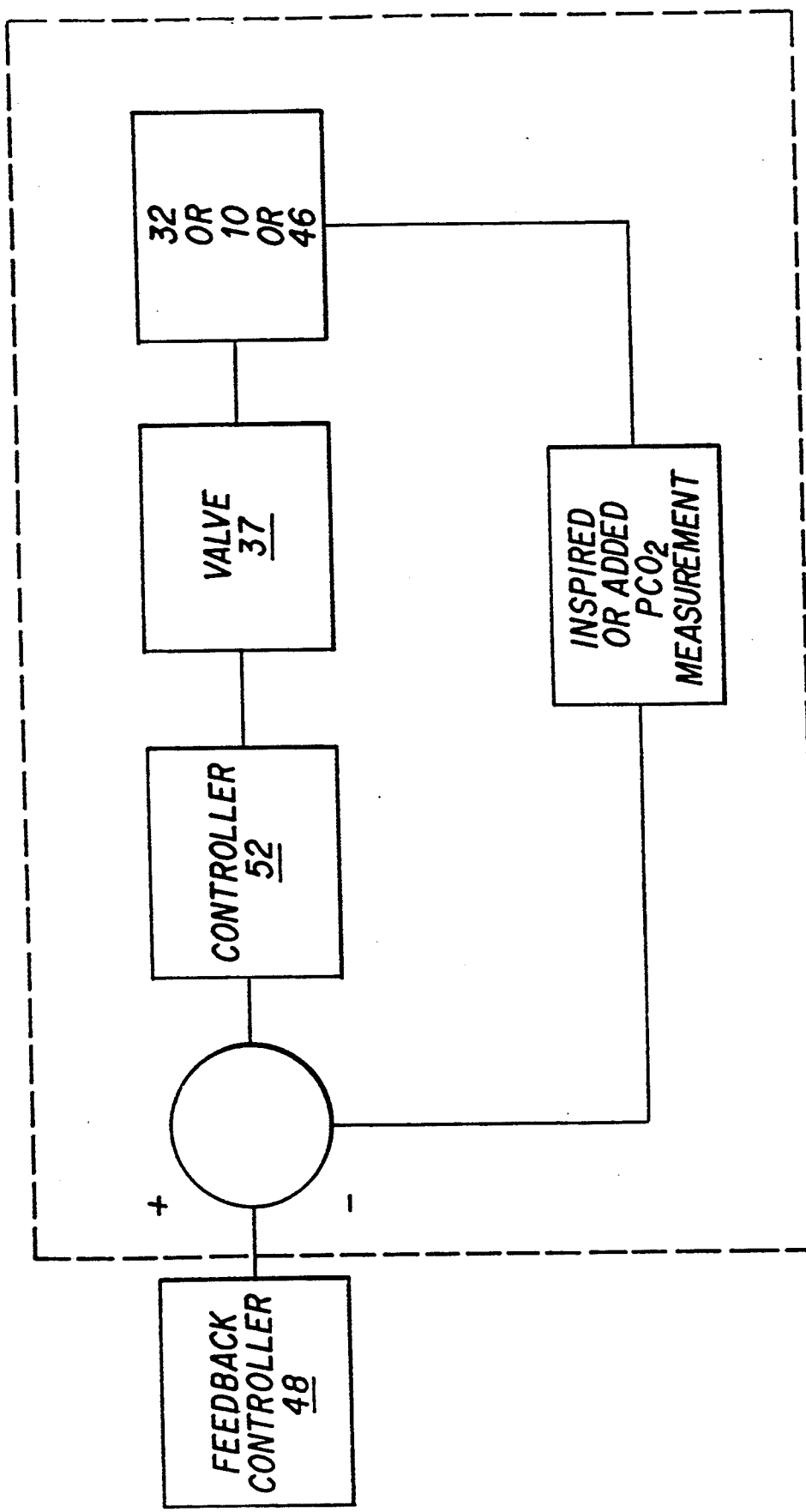
FIG. 4 is a block diagram of a $CO_{2ADD}$ actuator using secondary feedback for accuracy.

An additional feedback loop, as shown in FIG. 4, may also be used to increase accuracy. A measurement of the inspired or added $PCO_2$ can be compared to a reference value to adjust the $CO_2$ added into the breathing circuit. The inspired $CO_2$ may be also measured by the capnometer subsystem 46 while the added $CO_2$ may be measured in the mixing zone 32.

One of ordinary skill in the art will appreciate that there are a variety of controllers which can also be used in the closed-loop $PCO_2$ control. For example, good control in such a system can often be accomplished with just a PI controller (a controller with only proportional and integral terms), or a controller based upon bilinear transform, deadbeat, state feedback, optimal, linear digital regulator, digital state observer, minimal variance or the like.

The flow of $CO_2$ gas into the inspiration line 12 of circuit 10 may be controlled with a solenoid value which responds to the processor output. Alternatively, other controllable gas flow regulators can be used to control the flow of $CO_2$. For example, a mass flow controller, an electro-mechanically controlled needle valve, an electro-mechanically controlled pressure regulator and a fixed pneumatic resistance device can also be used to control the flow of $CO_2$.

A number of safety features may be incorporated in and made a part of the present invention. Generally, a safety subsystem is designated 56 in FIG. 1. For example, a flow measuring device, such as one which measures thermal dissipation, pressure difference across a resistive element, the rate of rotation of a vane or the oscillation frequency of a fluid vortex, may be used to measure the total fresh gas flow into the breathing circuit. The measurement of fresh gas flow within breathing circuit 10 is then compared with a fresh gas flow reference value of about 1 L/min. If the reference value exceeds the measured value of the fresh gas flow, the flow of $CO_2$ gas into breathing circuit 10 is inhibited.

Similarly, the concentration of oxygen $O_2$ within breathing circuit 10 can be measured and flow of $CO_2$ into the flow circuit is inhibited if the concentration of $O_2$ falls below a reference value. If the $O_2$ concentration falls below 21%, it is particularly critical to cease $CO_2$ addition. For additional safety, however, $CO_2$ addition should be stopped when the $O_2$ concentration falls below 30%.

Another safety system may be used in conjunction with the feedback control system which measures the average inspired carbon dioxide concentration within breathing circuit 10. If the average inspired $CO_2$ concentration exceeds a value of about 7%, no more $CO_2$ is introduced into the system. As with the other above described safety systems, $CO_2$ can be introduced into the system once the parameters within the breathing circuit dictate that it is safe to add $CO_2$. For example, once the concentration of $CO_2$ falls below the reference value, $CO_2$ can again be introduced into the breathing circuit.

Yet another safety system is the use of a device which detects the absence of breathing for a particular duration of time. If there is an absence of breathing, an alarm signals the anesthesiologist.

A series of safety features are implemented in the hardware and software to prevent hypoxic inspired mixtures and inadvertent operation of the system. These include:
1. System reset based on absence of $CO_2$ waveforms
2. System reset based on low FGF
3. $CO_{2ADD}$ disable based on pressure, flow, or electronic abnormality
4. System reset based on low $FIO_2$
5. Pneumatic and electronic "fail-off" design
6. Independent watch-dog microcomputer design strategy The submitted computer program, shown on the following two pages, demonstrates the digital PID controller for the $CO_2ADD$ system of the instant invention.

One of ordinary skill will appreciate that there are a large number of control mechanisms and breathing circuits which may be used in this invention. For example, *A Practice of Anaesthesia*, W. B. Saunders Co.: Philadelphia, 1978, pp. 110–118, herein incorporated by reference, discusses a number of breathing circuits which can be used in this invention. While the apparatus and method herein disclosed and described constitute preferred forms of the invention, it is to be understood that modifications and alterations within the spirit of the invention are anticipated, and that such mechanical arrangements and adaptations as fall within the scope of the claims are intended to be included herein.

I claim:
1. A method for restoring ventilatory drive to an anesthesized patient, the method comprising:
   (a) measuring the end-tidal value of the respiratory $PCO_2$ of the patient;
   (b) comparing said measurement of the end-tidal value of the respiratory $PCO_2$ with a reference value as feedback to determine the amount of $CO_2$ to be added to a patient's breathing circuit; and
   (c) adding said amount of $CO_2$ to the inspired mixture of the patient's breathing circuit.

2. The method of claim 1 wherein a device is used to detect the phases of a respiratory cycle.

3. The method of claim 2 wherein the $CO_2$ gas is added only during the inspired phase of the respiratory cycle.

4. The method of claim 3 wherein phases are detected by a flow meter.

5. The method of claim 1 further comprising the step of differentiating between the expired end-tidal $CO_2$ value and a inspired peak $CO_2$ value produced by the addition of $CO_2$ into the breathing mixture such that the effect of the inspired peak $CO_2$ value on the $CO_2$ addition is minimized.

6. The method of claim 1 wherein said feedback is determined by a term which is a function of difference between a desired and a measured $P_{ET}CO_2$.

7. The method of claim 1 wherein said feedback is determined by a term which is proportional to the time integral of the difference between a desired and a measured $P_{ET}CO_2$.

8. The method of claim 1 wherein said feedback is determined by a term which is proportional to the derivative with respect to time of the difference between a desired and a measured $P_{ET}CO_2$.

9. The method of claim 1 further comprising the step of controlling the time or the proportion of time a valve is left open to introduce the correct flow of $CO_2$ into the breathing mixture.

10. The method of claim 1 further comprising the step of measuring the total fresh gas flow into the subject's breathing circuit and inhibiting the addition of $CO_2$ gas into the circuit when the fresh gas flow is less than a particular value.

11. The method of claim 1 further comprising the step of measuring $O_2$ concentration within the breathing circuit and inhibiting $CO_2$ addition into the circuit when the $O_2$ concentration is less than a particular value.

12. The method of claim 1 further comprising the step of measuring the average inspired $CO_2$ concentration within the breathing circuit and inhibiting $CO_2$ addition into the circuit when the average inspired $CO_2$ concentration exceeds a particular value.

13. The method of claim 1 further comprising the step of detecting an absence of breathing for a particular duration of time and triggering an alarm upon said absence of breathing.

14. The method of claim 5 wherein the inspired peak value is greater than 2 mm Hg.

15. A device for restoring ventilatory drive to an anesthetized subject comprising:
   (a) means for determining the partial pressure of $CO_2$ in the blood stream of a subject;
   (b) feedback means utilizing said determination of the partial pressure of $CO_2$ in the blood stream of a subject; and
   (c) means for adding $CO_2$ into the breathing circuit as determined by the feedback means;
   (d) wherein said feedback means differentiates between the expired peak value of $CO_2$ from the inspired peak value of $CO_2$ which may be produced by the addition of $CO_2$ to the breathing mixture.

16. The method of claim 1 further comprising estimating the partial pressure of $CO_2$ within the patient's bloodstream by measuring the end-tidal value of the respiratory $PCO_2$.

17. The method of claim 1 wherein said feedback computes feedback compensation as a function of the difference between a desired value of $P_{ET}CO_2$ and the measured value of $P_{ET}CO_2$.

18. The method of claim 1 further comprising the step of comparing said added amount of $CO_2$ with a reference value to determine the amount of $CO_2$ to be added to the patient's breathing circuit.

19. The method of claim 1 further comprising the step of measuring the inspired $PCO_2$ and comparing the inspired amount of $CO_2$ with a reference value to determine the amount of $CO_2$ to be added to the patient's breathing circuit.

20. A device for restoring ventilatory drive to an anesthetized subject comprising:
   (a) means for determining the partial pressure of $CO_2$ in the blood stream of a subject;
   (b) feedback means utilizing said determination of the partial pressure of $CO_2$ in the blood stream of a subject; and
   (c) means for adding $CO_2$ into the breathing circuit as determined by the feedback means;
   (d) means for measuring the inspired $PCO_2$ of a subject and second feedback means for comparing said measured inspired $PCO_2$ with a reference value for determining the amount of $CO_2$ to be added into the breathing circuit.

21. A device for restoring ventilatory drive to an anesthetized subject comprising:
   (a) means for determining the partial pressure of $CO_2$ in the blood stream of a subject;
   (b) feedback means utilizing said determination of the partial pressure of $CO_2$ in the blood stream of a subject; and
   (c) means for adding $CO_2$ into the breathing circuit as determined by the feedback means;
   (d) means for comparing said added $CO_2$ with a reference value for determining the amount of $CO_2$ to be added into the breathing circuit.

* * * * *